United States Patent
Bhowmik et al.

(10) Patent No.: US 12,359,141 B2
(45) Date of Patent: Jul. 15, 2025

(54) POLYETHYLENEAMINE SALTS OF SULPHONYL OLEIC ACID AND DUAL FUNCTIONAL HYDROCARBON FUEL ADDITIVE COMPOSITION THEREOF

(71) Applicant: HINDUSTAN PETROLEUM CORPORATION LIMITED, Bengaluru (IN)

(72) Inventors: Sandip Bhowmik, Bengaluru (IN); Naresh Kottari, Bengaluru (IN); Chintalapati Siva Kesava Raju, Bengaluru (IN); Ramesh Kandanelli, Bengaluru (IN); Ravi Balasubramaniam, Bengaluru (IN)

(73) Assignee: Hindustan Petroleum Corporation Limited, Bengaluru (IN)

( * ) Notice: Subject to any disclaimer, the term of this patent is extended or adjusted under 35 U.S.C. 154(b) by 0 days.

(21) Appl. No.: 18/274,099

(22) PCT Filed: Sep. 15, 2021

(86) PCT No.: PCT/IN2021/050908
§ 371 (c)(1),
(2) Date: Jul. 25, 2023

(87) PCT Pub. No.: WO2022/201171
PCT Pub. Date: Sep. 29, 2022

(65) Prior Publication Data
US 2024/0417638 A1 Dec. 19, 2024

(30) Foreign Application Priority Data
Mar. 20, 2021 (IN) .............................. 202141011960

(51) Int. Cl.
*C10L 10/08* (2006.01)
*C07C 211/14* (2006.01)
(Continued)

(52) U.S. Cl.
CPC .......... *C10L 1/2437* (2013.01); *C07C 211/14* (2013.01); *C07C 309/22* (2013.01);
(Continued)

(58) Field of Classification Search
CPC ...... C10L 1/2437; C10L 1/1855; C10L 10/08; C10L 2200/0446; C10L 2230/20; C10L 2270/026; C07C 211/14; C07C 309/22
See application file for complete search history.

(56) References Cited

U.S. PATENT DOCUMENTS 2,329,086 A * 9/1943 Robinson ............... D21H 17/09
252/8.63
3,085,867 A * 4/1963 Fareri ................... C10L 1/2425
44/371
(Continued)

OTHER PUBLICATIONS

Homa Hosseinzadeh-Bandbafha et al "Energy Conversion and Management" Energy Conversion and Management 174 (2018) 579-614, © 2018 Elsevier Ltd., https://doi.org/10.1016/j.enconman.2018.08.050.

*Primary Examiner* — Ellen M McAvoy
*Assistant Examiner* — Chantel Graham
(74) *Attorney, Agent, or Firm* — The Belles Group, P.C.

(57) ABSTRACT

The present invention discloses polyethyleneamine salts of sulphonyl oleic acid and a 5 hydrocarbon fuel additive composition comprising the same. The said polyethyleneamine salts of sulphonyl oleic acid is made by mixing a sulphonyl oleic acid with at least one polyethyleneamine. Wherein, the sulphonyl oleic acid is selected from at least one of (9Z)-8-sulfo-octadec-9-enoic acid or (9Z)-11-sulfo-octadec-9-enoic acid. The at least one polyethyleneamine is selected from triethylenetetramine (TETA), or diethylenetriamine 0 (DETA), pentamethyldiethylenetriamine, tetraethylenepentamine, 1,4,7-triazacyclononane, 1,1,1-Tris(aminomethyl)ethane, or cyclen. The hydrocarbon fuel additive
(Continued)

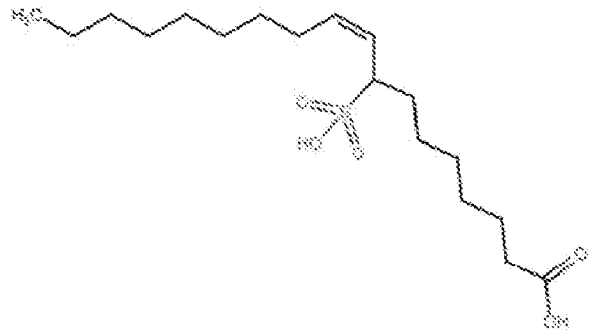

(9Z)-8-sulfo-octadec-9-enoic acid composition is made of polyethyleneamine salts of sulphonyl oleic acid and a cosolvent system consisting of sulphonyl oleic acid and dioxane. Wherein, the said hydrocarbon fuel additive composition acts as a dual functional additive and synergistically improves the conductivity as well as 5 lubricity of a hydrotreated diesel fuel.

10 Claims, 3 Drawing Sheets

(51) Int. Cl.
    *C07C 309/22*     (2006.01)
    *C10L 1/185*     (2006.01)
    *C10L 1/24*     (2006.01)

(52) U.S. Cl.
    CPC ............ *C10L 1/1855* (2013.01); *C10L 10/08* (2013.01); *C10L 2200/0446* (2013.01); *C10L 2230/20* (2013.01); *C10L 2270/026* (2013.01)

(56) References Cited

U.S. PATENT DOCUMENTS

| | | | |
|---|---|---|---|
| 4,478,642 A | * | 10/1984 | Schilling .................... C08J 3/03 |
| | | | 106/277 |
| 6,793,695 B2 | | 9/2004 | Wilkes et al. |
| 8,287,608 B2 | | 10/2012 | Schwab |
| 10,308,899 B2 | | 6/2019 | Nielsen et al. |

* cited by examiner

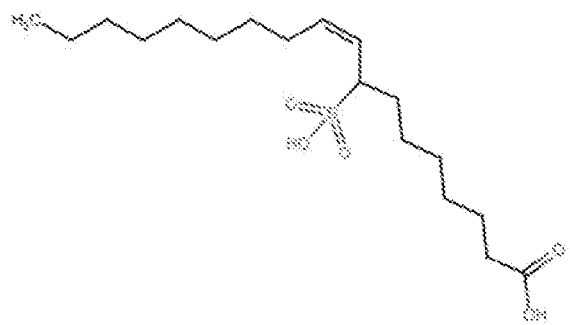
Fig. 1A: (9Z)-8-sulfo-octadec-9-enoic acid
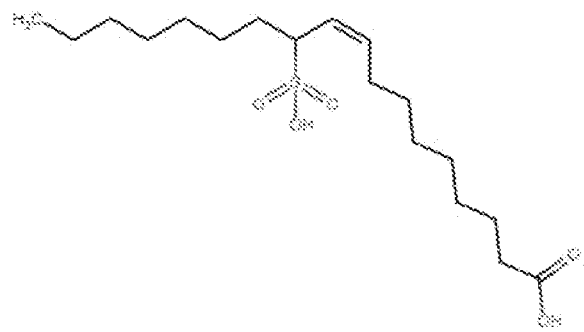
Fig. 1B: (9Z)-11-sulfo-octadec-9-enoic acid

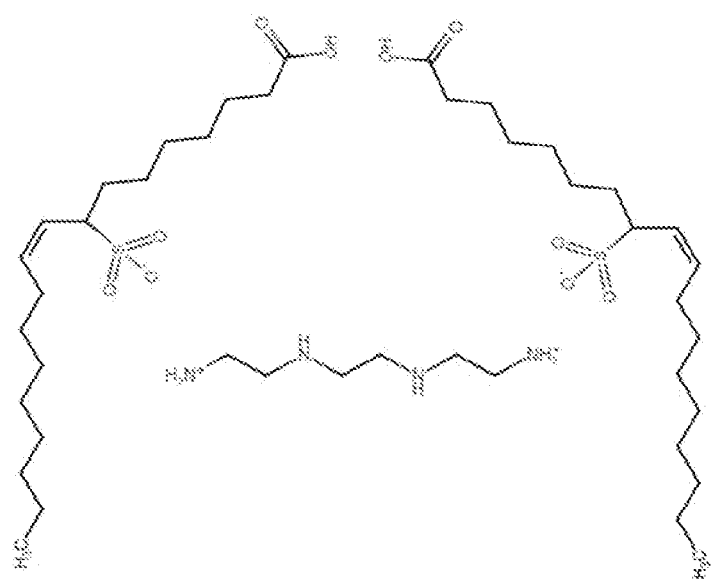
Fig. 2: Salt of (9Z)-8-sulfo-octadec-9-enoic with TETA

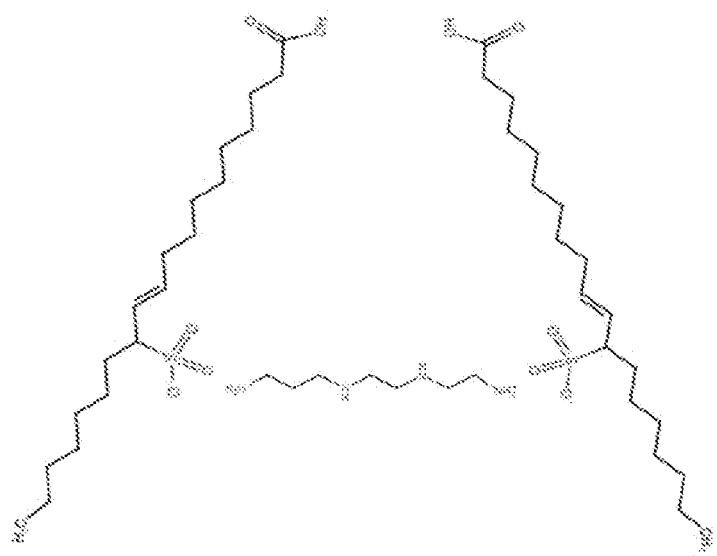
Fig. 3: Salt of (9Z)-11-sulfo-octadec-9-enoic with TETA

POLYETHYLENEAMINE SALTS OF SULPHONYL OLEIC ACID AND DUAL FUNCTIONAL HYDROCARBON FUEL ADDITIVE COMPOSITION THEREOF

CROSS-REFERENCE TO RELATED PATENT APPLICATIONS

The present application is a U.S. national stage application under 35 U.S.C. § 371 of PCT/IN2021/050908, filed Sep. 15, 2021, which claims priority to Indian Patent Application number 202141011960 filed on Mar. 20, 2021. The disclosures of the aforementioned priority applications are incorporated herein by reference.

FIELD OF THE INVENTION

The present invention relates to polyethyleneamine salts of sulphonyl oleic acid and preparation thereof. Further, the present invention provides a hydrocarbon fuel additive composition comprising the said polyethyleneamine salts of sulphonyl oleic acid along with sulphonyl oleic acid and dioxane. Further, the present invention also relates to the process for preparing the said additive compositions. Especially, the present invention relates to hydrocarbon fuel additive compositions for improving conductivity and lubricity of a hydrotreated diesel fuel such as Ultra-Low Sulfur Diesel (ULSD).

BACKGROUND OF THE INVENTION

While processing and transporting the liquid hydrocarbon fuels, the continuous contact and friction of hydrocarbon molecules with the container surfaces generate static charge.

Sometime, the said static charge can produce spark and thus, cause disastrous accidents. The hydrocarbon fuel conductivity is an important property as it prevents creation of static charge during rapid movement like transportation and processing. Similarly, lubricity is also considered as an important property of the hydrocarbon fuels as lubricity prevents wear-related damages.

Further, due to environmental concerns, the hydrocarbon fuels such as diesel are hydrotreated to reduce Sulfur and Nitrogen content resulting in fuels such as Ultra-Low Sulfur Diesel (ULSD). Further, the reduced Sulfur and Nitrogen content affects the electrical conductivity of diesel. At the same time, the Euro VI standard specification for minimum diesel conductivity is set at 25 pS/m which is considered safe for transportation and operations purposes. Thus, to improve the electrical conductivity the antistatic additives are added in the said Ultra-Low Sulfur Diesel (ULSD).

Similarly, the hydrotreatment of diesel also impacts the lubricity negatively and external additives are added to restore the lubricity. Some of such known additives are discussed hereinbelow.

U.S. Pat. No. 6,793,695B2 discloses a fuel composition exhibiting improved anti-static properties, comprising a liquid fuel which contains less than 500 parts per million by weight sulfur; 0.001 to 1 ppm of a hydrocarbyl monoamine or hydrocarbyl-substituted poly(alkyleneamine); and 10 to 500 ppm of at least one fatty acid containing 8 to 24 carbon atoms, or an ester thereof.

U.S. Pat. No. 8,287,608B2 discloses a lubricity additive for low sulfur fuels. The said lubricity additive is a mixture of an amine having at least one alicyclic group and a monocarboxylic acid having up to 22 carbon atoms. Specifically, the said lubricity additive includes a liquid mixture of about 5 to about 30 weight percent of N,N-dimethylcyclohexylamine and one or more unsaturated monocarboxylic acid(s) selected from the group consisting of oleic acid, and tall oil fatty acid. The liquid mixture is substantially free of an amide reaction product between the N,N-dimethylcyclohexylamine and the one or more unsaturated monocarboxylic acid(s). Further, the said liquid mixture exhibits a depressed cloud point temperature of about 1.9° C. or below relative to a cloud point temperature of the one or more monocarboxylic acid(s).

U.S. Ser. No. 10/308,889B1 discloses a lubricity additive for fuels. The said additive comprising a lubricity additive mixture of (i) at least one neutral lubricity additive prepared by reacting a hydrocarbyl-substituted succinic anhydride with ammonia, wherein, the hydrocarbyl substituent includes 8 to 20 carbons and (ii) at least one linear monocarboxylic acid or salt thereof having a carbon chain of 16 to 20 carbons. Wherein, the linear monocarboxylic acid or salt thereof being saturated, unsaturated, or including mixtures thereof.

However, these additive formulations often comprise of individual molecular components that independently improve either or both conductivity and lubricity but none that can do both through a single molecular species. Furthermore, such additives should also resolve the frequent issue of loss of conductivity over longer periods due to stability, precipitation, and absorption related phenomenon.

Objective of the Present Invention

The objective of the present invention is to provide a single molecular species which shows dual functionality by improving both the lubricity as well as the conductivity of the Ultra-Low Sulfur Diesel (ULSD). Wherein, the said single molecular species shows excellent conductivity and lubricity improvement via a synergistic reinforcement of individual properties.

The other objective of the present invention is to provide a hydrocarbon fuel additive composition which improves the lubricity as well as the conductivity of the Ultra-Low Sulfur Diesel (ULSD).

Another objective of the present invention is to provide a process for preparing the said single molecular species and hydrocarbon fuel additive composition thereof which improves both the lubricity as well as the conductivity of Ultra-Low Sulfur Diesel (ULSD).

SUMMARY OF THE INVENTION

The present invention discloses polyethyleneamine salt(s) of sulphonyl oleic acid and a hydrocarbon fuel additive composition thereof which gives dual functionality of improving the conductivity as well as lubricity of a hydrotreated diesel fuel. The polyethyleneamine salt(s) of sulphonyl oleic acid as disclosed in the present invention is a single molecular species. Further, the polyethyleneamine salt(s) of sulphonyl oleic acid and the said hydrocarbon fuel additive composition thereof enhances the lubricity and the antistatic properties of Ultra Low Sulfur Diesel (ULSD).

The dual functional groups of the said polyethyleneamine salt(s) of sulphonyl oleic acid acts as conductivity and lubricity improver.

Further, the presence of carboxylic acid on the polyethyleneamine salt structure significantly improves the solubility in the presence of a cosolvent system consisting of sulphonyl oleic acid and dioxane.

Further, the said hydrocarbon fuel additive composition comprises sulphonyl oleic acid, dioxane and the said polyethyleneamine salt(s) of sulphonyl oleic acid. Wherein, the said polyethyleneamine salt(s) of sulphonyl oleic acid includes a sulphonyl oleic acid and at least one polyethyleneamine.

The sulphonyl oleic acid is selected from one of (9Z)-8-sulfo-octadec-9-enoic acid, (9Z)-11-sulfo-octadec-9-enoic acid or a combination thereof. The said at least one polyethyleneamine is selected from but not limited to triethylenetetramine (TETA), diethylenetriamine (DETA), pentamethyldiethylenetriamine, tetraethylenepentamine, 1,4,7-triazacyclononane, 1,1,1-Tris(aminomethyl)ethane, or cyclen.

Furthermore, the said hydrocarbon fuel additive composition has long-term stability and solubility in Ultra-Low Sulfur Diesel (ULSD).

The present invention also discloses a process for preparing the said hydrocarbon fuel additive composition having dual functionality. The first step includes preparing at least one polyethyleneamine salt of sulphonyl oleic acid by mixing sulphonyl oleic acid with at least one polyethyleneamine. Wherein, the sulphonyl oleic acid is in a range of 71-75% by volume and at least one polyethyleneamine is in a range of 25-29% by volume. The fuel additive composition is then prepared by mixing (i) 95-99% by weight of a sulphonyl oleic acid; (ii) 0.5-2.5% by weight of dioxane and (iii) 0.5-2.5% by weight of polyethyleneamine salt of a sulphonyl oleic acid.

The final fuel composition is then prepared by contacting the aforementioned additive composition with Ultra Low Sulfur Diesel fuel (ULSD), wherein the said fuel additive concentration in the ULSD is in the range of 40-125 ppm.

DESCRIPTION OF THE DRAWINGS

To further clarify advantages and aspects of the invention, a more particular description of the invention will be rendered by reference to specific embodiments thereof, which is illustrated in the appended drawing(s). It is appreciated that the drawing(s) of the present invention depicts only typical embodiments of the invention and are therefore not to be considered limiting of its scope.

FIG. 1A: Illustrates molecular structure of (9Z)-8-sulfo-octadec-9-enoic acid;

FIG. 1B: Illustrates molecular structure of (9Z)-11-sulfo-octadec-9-enoic acid;

FIG. 2: Illustrates salt of (9Z)-8-sulfo-octadec-9-enoic with TETA; and

FIG. 3: Illustrates salt of (9Z)-11-sulfo-octadec-9-enoic with TETA.

DETAILED DESCRIPTION OF THE INVENTION

For promoting an understanding of the principles of the present disclosure, reference will now be made to the specific embodiments of the present invention further illustrated in the drawings and specific language will be used to describe the same. The foregoing general description and the following detailed description are explanatory of the present disclosure and are not intended to be restrictive thereof. It will nevertheless be understood that no limitation of the scope of the present disclosure is thereby intended, such alterations and further modifications in the illustrated composition, and such further applications of the principles of the present disclosure as illustrated herein being contemplated as would normally occur to one skilled in the art to which the present disclosure relates. Unless otherwise defined, all technical and scientific terms used herein have the same meaning as commonly understood by one of ordinarily skilled in the art to which this present disclosure belongs. The methods, and examples provided herein are illustrative only and not intended to be limiting.

The present invention discloses polyethyleneamine salt(s) of sulphonyl oleic acid and a hydrocarbon fuel additive composition thereof which improves both the lubricity as well as the conductivity of Ultra-Low Sulfur Diesel fuels. The polyethyleneamine salt(s) of a sulphonyl carboxylic acid as disclosed in the present invention is a single molecular species.

The hydrocarbon fuel additive composition as disclosed in the present invention consists the said polyethyleneamine salt(s) of the sulphonyl oleic acid. The said polyethyleneamine salt(s) of sulphonyl oleic acid simultaneously acts as a conductivity and lubricity improver through the dual functional groups.

In an embodiment, the present invention discloses a hydrocarbon fuel additive composition which shows dual functionality of improving the conductivity as well as lubricity of a hydrotreated diesel fuel. Specifically, the said composition is used for enhancing the lubricity and the antistatic properties of Ultra Low Sulfur Diesel (ULSD).

Specifically, the said composition comprises sulphonyl oleic acid, dioxane and polyethyleneamine salt(s) of sulphonyl oleic acid. The said polyethyleneamine salt(s) of sulphonyl oleic acid is made up of sulphonyl oleic acid and at least one polyethyleneamine. The sulphonyl oleic acid is selected from one of (9Z)-8-sulfo-octadec-9-enoic acid, (9Z)-11-sulfo-octadec-9-enoic acid or a combination thereof. The said at least one polyethyleneamine is one of but not limited to triethylenetetramine (TETA), diethylenetriamine (DETA) pentamethyldiethylenetriamine, tetraethylenepentamine, 1,4,7-triazacyclononane, 1,1,1-Tris(aminomethyl)ethane, or cyclen. The sulphonyl oleic acid is selected from one of (9Z)-8-sulfo-octadec-9-enoic acid or (9Z)-11-sulfo-octadec-9-enoic acid.

The presence of carboxylic acid on the molecular backbone of the said polyethyleneamine salt increases both lubricity and conductivity. Furthermore, it also ensures significantly improved solubility in the presence of a cosolvent system consisting of sulphonyl oleic acid and dioxane, thus, improving long-term stability of the additive in diesel.

Specifically, the present invention provides a hydrocarbon fuel additive composition containing (i) 95-99% by weight of a sulphonyl oleic acid; (ii) 0.5-2.5% by weight of dioxane; (iii) 0.5-2.5% by weight of polyethyleneamine salt of sulphonyl oleic acid.

The present invention also discloses a process for preparing a hydrocarbon fuel additive composition having dual functionality. The first step includes preparing at least one polyethyleneamine salt of sulphonyl oleic acid by mixing sulphonyl oleic acid with at least one polyethyleneamine. Wherein, the sulphonyl oleic acid is in a range of 71-75% by volume and at least one polyethyleneamine is in a range of 25-29% by volume. The final hydrocarbon fuel additive composition is then prepared by mixing (i) 95-99% by weight of a sulphonyl oleic acid; (ii) 0.5-2.5% by weight of dioxane and (iii) 0.5-2.5% by weight of polyethyleneamine salt of sulphonyl oleic acid.

The present invention also discloses a method for enhancing lubricity and conductivity of a hydrocarbon fuel, wherein, the method comprising, mixing the hydrocarbon fuel additive composition claimed in claim 2-5 with the said hydrocarbon fuel to obtain a hydrocarbon fuel composition with enhanced lubricity and conductivity.

Specifically, the fuel composition is then prepared by contacting the aforementioned additive composition with Ultra Low Sulfur Diesel fuel (ULSD), wherein the additive concentration in the ULSD is in the range of 40-125 ppm. Wherein, the Ultra Low Sulfur Diesel having sulfur content in the range of 0-10 ppm.

The sulphonyl oleic acid as used herein is selected from at least one of (9Z)-8-sulfo-octadec-9-enoic acid, (9Z)-11-sulfo-octadec-9-enoic acid or a combination thereof.

The said at least one polyethyleneamine is one of but not limited to triethylenetetramine (TETA), diethylenetriamine (DETA) pentamethyldiethylenetriamine, tetraethylenepentamine, 1,4,7-triazacyclononane, 1,1,1-Tris(aminomethyl) ethane, or cyclen.

Further, the said polyethyleneamine salt of sulphonyl oleic acid is prepared by mixing (9Z)-8-sulfo-octadec-9-enoic acid with triethylenetetramine (TETA). Wherein, the said (9Z)-8-sulfo-octadec-9-enoic acid is 71% by volume and triethylenetetramine (TETA) is 29% by volume. The final hydrocarbon fuel additive composition is then prepared by mixing (i) 95-99% by weight of (9Z)-8-sulfo-octadec-9-enoic acid; (ii) 0.5-2.5% by weight of dioxane and (iii) 0.5-2.5% by weight of triethylenetetramine salt of (9Z)-8-sulfo-octadec-9-enoic acid. The fuel composition is then prepared by contacting the aforementioned additive composition with Ultra Low Sulfur Diesel fuel (ULSD), wherein the additive concentration in the ULSD is in the range of 40-125 ppm.

Further, the said polyethyleneamine salt of sulphonyl oleic acid is prepared by mixing (9Z)-8-sulfo-octadec-9-enoic acid with diethylenetriamine (DETA). Wherein, the said (9Z)-8-sulfo-octadec-9-enoic acid is 75% by volume and diethylenetriamine (DETA) is 25% by volume. The final hydrocarbon fuel additive composition is then prepared by mixing (i) 95-99% by weight of (9Z)-8-sulfo-octadec-9-enoic acid; (ii) 0.5-2.5% by weight of dioxane and (iii) 0.5-2.5% by weight of diethylenetriamine salt of (9Z)-8-sulfo-octadec-9-enoic acid. The fuel composition is then prepared by contacting the aforementioned additive composition with Ultra Low Sulfur Diesel fuel (ULSD), wherein the additive concentration in the ULSD is in the range of 40-125 ppm.

Further, the said polyethyleneamine salt of sulphonyl oleic acid is prepared by mixing (9Z)-11-sulfo-octadec-9-enoic acid with triethylenetetramine (TETA). Wherein, the said (9Z)-11-sulfo-octadec-9-enoic acid is 71% by volume and triethylenetetramine (TETA) is 29% by volume. The final hydrocarbon fuel additive composition is then prepared by mixing (i) 95-99% by weight of (9Z)-11-sulfo-octadec-9-enoic acid; (ii) 0.5-2.5% by weight of dioxane and (iii) 0.5-2.5% by weight of triethylenetetramine salt of (9Z)-11-sulfo-octadec-9-enoic acid. The fuel composition is then prepared by contacting the aforementioned additive composition with Ultra Low Sulfur Diesel fuel (ULSD), wherein the additive concentration in the ULSD is in the range of 40-125 ppm.

Furthermore, the said polyethyleneamine salt of sulphonyl oleic acid is prepared by mixing (9Z)-11-sulfo-octadec-9-enoic acid with diethylenetriamine (DETA). Wherein, the said (9Z)-11-sulfo-octadec-9-enoic acid is 75% by volume and diethylenetriamine (DETA) is 25% by volume. The final hydrocarbon fuel additive composition is then prepared by mixing (i) 95-99% by weight of (9Z)-11-sulfo-octadec-9-enoic acid; (ii) 0.5-2.5% by weight of dioxane and (iii) 0.5-2.5% by weight of diethylenetriamine salt of (9Z)-11-sulfo-octadec-9-enoic acid. The fuel composition is then prepared by contacting the aforementioned additive composition with Ultra Low Sulfur Diesel fuel (ULSD), wherein the additive concentration in the ULSD is in the range of 40-125 ppm.

Examples of preparation of test samples for conductivity and lubricity measurements are provided hereinbelow.

Example 1

In an exemplary embodiment, 0.1 mL of triethylenetetramine (TETA) and 0.25 mL of (9Z)-8-sulfo-octadec-9-enoic acid both are mixed with each other to form solid Salt-1. Further, 10 mg of the said Salt-1 and 20 µL of dioxane are then dissolved in 1 mL of (9Z)-8-sulfo-octadec-9-enoic acid to form the standard solution. 120 µL of the above standard solution is diluted in 1 Litre of hydrotreated diesel to form the test solution (Sr. no. 5 in Table 1).

Example 2

In another exemplary embodiment, 0.1 mL of diethylenetriamine (DETA) and 0.3 mL of (9Z)-8-sulfo-octadec-9-enoic acid are mixed with each other to form solid Salt-2. Further, 10 mg of the said Salt-2 and 20 µL of dioxane are then dissolved in 1 mL of (9Z)-8-sulfo-octadec-9-enoic acid to form the standard solution. 120 µL of the above standard solution is diluted in 1 Litre of hydrotreated diesel to form the test solution (Sr. no. 18 in Table 1).

Example 3

In another exemplary embodiment, 0.1 mL of triethylenetetramine (TETA) and 0.25 mL of (9Z)-11-sulfo-octadec-9-enoic acid both are mixed with each other to form solid Salt-3. Further, 10 mg of the said Salt-3 and 20 µL of dioxane are then dissolved in 1 mL of (9Z)-11-sulfo-octadec-9-enoic acid to form the standard solution. 120 µL of the above standard solution is diluted in 1 Litre of hydrotreated diesel to form the test solution (Sr. no. 23 in Table 1).

Methodology for Measuring Conductivity & Lubricity:

Conductivity measurements of the above test samples are carried out as per ASTM D2624. The synergistic effects of antistatic additive on lubricity are established through High Frequency Reciprocating Rig (HFRR) measurements as per ASTM D6079.

Comparative Data and Experimental Results:

The experimental results and comparative data are listed in below tables to identify the advantages of the single molecular species and the hydrocarbon fuel additive composition thereof as disclosed in the present invention. Wherein, the said single molecular species shows dual functionality of improving the conductivity as well as lubricity of a hydrotreated diesel fuel. The single molecular species as disclosed herein is a unique polyethyleneamine salts of a sulphonyl carboxylic acid as herein represented Salt-1, Salt-2, and Salt-3.

TABLE 1

Conductivity Measurement

| Sr. No. | (9Z)-8-sulfo-octadec-9-enoic acid (ppm) | (9Z)-11-sulfo-octadec-9-enoic acid (ppm) | Dioxane (ppm) | Salt-1 (ppm) | Salt-2 (ppm) | Salt-3 (ppm) | Ultra-Low Sulfur Diesel (%) | Conductivity (pS/m) |
|---|---|---|---|---|---|---|---|---|
| 1. | 120 | 0 | 0 | 0 | 0 | 0 | 99.98 | 29 |
| 2. | 0 | 0 | 120 | 0 | 0 | 0 | 99.98 | 0 |
| 3. | 120 | 0 | 2.4 | 0 | 0 | 0 | 99.98 | 28 |
| 4. | 120 | 0 | 2.4 | 0.5 | 0 | 0 | 99.98 | 83 |
| 5. | 120 | 0 | 2.4 | 1.0 | 0 | 0 | 99.98 | 117 |
| 6. | 120 | 0 | 2.4 | 1.2 | 0 | 0 | 99.98 | 144 |
| 7. | 120 | 0 | 2.4 | 1.5 | 0 | 0 | 99.98 | 164 |
| 8. | 120 | 0 | 2.4 | 1.75 | 0 | 0 | 99.98 | 173 |
| 9. | 120 | 0 | 2.4 | 2.0 | 0 | 0 | 99.98 | 188 |
| 10. | 0 | 0 | 0 | 1.2 | 0 | 0 | 99.98 | 15 |
| 11 | 120 | 0 | 0 | 1.2 | 0 | 0 | 99.98 | 119 |
| 12. | 120 | 0 | 1.0 | 1.2 | 0 | 0 | 99.98 | 127 |
| 13. | 120 | 0 | 3.0 | 1.2 | 0 | 0 | 99.98 | 148 |
| 14. | 40 | 0 | 2.4 | 1.2 | 0 | 0 | 99.98 | 149 |
| 15. | 80 | 0 | 2.4 | 1.2 | 0 | 0 | 99.98 | 141 |
| 16. | 120 | 0 | 2.4 | 0 | 0.5 | 0 | 99.98 | 69 |
| 17. | 120 | 0 | 2.4 | 0 | 1.0 | 0 | 99.98 | 103 |
| 18. | 120 | 0 | 2.4 | 0 | 1.2 | 0 | 99.98 | 138 |
| 19. | 120 | 0 | 2.4 | 0 | 1.5 | 0 | 99.98 | 141 |
| 20. | 120 | 0 | 2.4 | 0 | 1.75 | 0 | 99.98 | 153 |
| 21. | 120 | 0 | 2.4 | 0 | 2.0 | 0 | 99.98 | 147 |
| 22. | 0 | 120 | 0 | 0 | 0 | 0 | 99.98 | 26 |
| 23. | 0 | 120 | 2.4 | 0 | 0 | 0.5 | 99.98 | 88 |
| 24. | 0 | 120 | 2.4 | 0 | 0 | 1.2 | 99.98 | 123 |
| 25. | 0 | 120 | 2.4 | 0 | 0 | 1.5 | 99.98 | 135 |
| 26. | 0 | 120 | 2.4 | 0 | 0 | 2.0 | 99.98 | 144 |
| 27. | 0 | 120 | 1.0 | 0 | 0 | 1.2 | 99.98 | 119 |
| 28. | 0 | 120 | 3.0 | 0 | 0 | 1.2 | 99.98 | 128 |

The observations as made from above conductivity measurement data are presented hereinafter. The base diesel shows negligible conductivity in absence of any additive. Further, the above conductivity measurement data proves that Salt-1, Salt-2, and Salt-3 significantly improves the conductivity of the base diesel.

Further, it is also observed that if the Salt-1, Salt-2, and Salt-3 are directly dissolved into the base diesel then only negligible improvements are observed. Moreover, considerable improvement in diesel conductivity is only noticed when the said salts are diluted with either of the sulphonyl oleic acid and dioxane mixture before dissolving in diesel.

It is to be noted that the above-mentioned salts have poor solubility in diesel and are not soluble beyond 10 ppm, whereas the solubility increases significantly with sulphonyl oleic acid and dioxane.

Further, it is also noticed that the conductivity increases with increasing the salt concentration (Sr. no. 4-9 for Salt-1, Sr. no. 16-21 for Salt-2 and Sr. no. 23-28 for Salt-3 in Table 1). It is also observed that both the sulphonyl oleic acids i.e. (9Z)-8-sulfo-octadec-9-enoic acid, or (9Z)-11-sulfo-octadec-9-enoic acid individually increases the conductivity of diesel to a moderate extent. However, there is no such effect provided by dioxane.

Similarly, lubricity measurement for Salt-1, Salt-2 and Salt-3 is also conducted, and lubricity measurement data is represented in below table 2.

TABLE 2

Lubricity measurement

| Sr. No. | (9Z)-8-sulfo-octadec-9-enoic acid (ppm) | (9Z)-11-sulfo-octadec-9-enoic acid (ppm) | Dioxane (ppm) | Salt-1 (ppm) | Salt-2 (ppm) | Salt-3 (ppm) | Ultra-Low Sulfur Diesel (%) | Average Wear Scar Diameter (μM) |
|---|---|---|---|---|---|---|---|---|
| 1. | 0 | 0 | 0 | 0 | 0 | 0 | 99.98 | 671 |
| 2. | 0 | 120 | 0 | 0 | 0 | 0 | 99.98 | 416 |
| 3. | 0 | 0 | 120 | 0 | 0 | 0 | 99.98 | 688 |
| 4. | 0 | 0 | 0 | 2.0 | 0 | 0 | 99.98 | 677 |
| 5. | 0 | 120 | 2.4 | 0 | 0 | 0 | 99.98 | 421 |
| 6. | 0 | 120 | 2.4 | 0.5 | 0 | 0 | 99.98 | 411 |
| 7. | 0 | 120 | 2.4 | 1.0 | 0 | 0 | 99.98 | 405 |
| 8. | 0 | 120 | 2.4 | 1.2 | 0 | 0 | 99.98 | 397.5 |
| 9. | 0 | 120 | 2.4 | 1.5 | 0 | 0 | 99.98 | 393 |
| 10. | 0 | 120 | 2.4 | 1.75 | 0 | 0 | 99.98 | 401 |
| 11. | 0 | 120 | 2.4 | 2.0 | 0 | 0 | 99.98 | 395.5 |
| 12. | 0 | 40 | 2.4 | 1.2 | 0 | 0 | 99.98 | 588.5 |
| 13. | 0 | 80 | 2.4 | 1.2 | 0 | 0 | 99.98 | 498.5 |

TABLE 2-continued

Lubricity measurement

| Sr. No. | (9Z)-8-sulfo-octadec-9-enoic acid (ppm) | (9Z)-11-sulfo-octadec-9-enoic acid (ppm) | Dioxane (ppm) | Salt-1 (ppm) | Salt-2 (ppm) | Salt-3 (ppm) | Ultra-Low Sulfur Diesel (%) | Average Wear Scar Diameter (μM) |
|---|---|---|---|---|---|---|---|---|
| 14. | 0 | 100 | 2.4 | 1.2 | 0 | 0 | 99.98 | 461 |
| 15. | 0 | 120 | 1 | 1.2 | 0 | 0 | 99.98 | 421 |
| 16. | 0 | 120 | 2.4 | 1.2 | 0 | 0 | 99.98 | 419.5 |
| 17. | 0 | 120 | 3 | 1.2 | 0 | 0 | 99.98 | 410 |
| 18. | 0 | 120 | 2.4 | 0 | 1.2 | 0 | 99.98 | 389 |
| 19. | 40 | 0 | 2.4 | 0 | 0 | 1.2 | 99.98 | 593 |
| 20 | 80 | 0 | 2.4 | 0 | 0 | 1.2 | 99.98 | 507 |
| 21. | 100 | 0 | 2.4 | 0 | 0 | 1.2 | 99.98 | 456 |
| 22. | 120 | 0 | 1 | 0 | 0 | 1.2 | 99.98 | 408 |

The observations as made from above lubricity measurement data shows that the dioxane does not have any independent impact on the lubricity of the diesel. It is also observed that at low concentration the above-mentioned salts have slight impact on the lubricity of the diesel.

Further, it is also observed that the lubricity improves with increasing concentration of both the sulphonyl oleic acid i.e. (9Z)-8-sulfo-octadec-9-enoic acid (Sr. No 1-18 in Table 2), or (9Z)-11-sulfo-octadec-9-enoic acid (Sr. No 19-22 in Table 2).

Moreover, it is also observed that the Salt-1, Salt-2, and Salt-3 improves the diesel lubricity through positive synergistic effect in presence of sulphonyl oleic acids i.e. (9Z)-8-sulfo-octadec-9-enoic acid, and/or (9Z)-11-sulfo-octadec-9-enoic acid.

Stability Studies:

It is very commonly experienced as well as documented in literature that hydrocarbon fuel additive conductivity reduces with time, presumably, because of opposite ions associating and neutralizing gradually.

Thus, it is important and necessary to profile the conductivity change over time. The results (as mentioned below in table 3) clearly demonstrate the superior performance of the hydrocarbon fuel additive compositions as provided by the present invention.

TABLE 3

Variation of conductivity with time

| Sr. No. | Sample Name | Concentration of additive (ppm) | Day of testing | Conductivity (pS/m) @24.4° C. |
|---|---|---|---|---|
| 1. | Example 1 | (9Z)-8-sulfo-octadec-9-enoic acid: 120 ppm Salt-1: 1.2 ppm Dioxane: 2.4 ppm | Day 1 Day 14 Day 30 Day 39 | 144.7 124.8 101.5 80.6 |
| 2. | Example 2 | (9Z)-8-sulfo-octadec-9-enoic acid: | Day 1 Day 14 | 142 117.8 |

TABLE 3-continued

Variation of conductivity with time

| Sr. No. | Sample Name | Concentration of additive (ppm) | Day of testing | Conductivity (pS/m) @24.4° C. |
|---|---|---|---|---|
| | | 120 ppm Salt-2: 1.2 ppm Dioxane: 2.4 ppm | Day 30 Day 39 | 89.2 70 |

Further, it is also noted that temperature critically impacts the conductivity of the hydrotreated diesel fuel. Thus, it is important and necessary to determine the impact of temperature on the conductivity of the hydrotreated diesel fuel having hydrocarbon fuel additive compositions as provided by the present invention.

Accordingly, in below table 4, the effect of temperature is also probed in working temperature range of 15-40° C. For the temperature variation studies, the same aged samples (39 day old) are used.

TABLE 4

Effect of temperature on conductivity

| | | CONDUCTIVITY (pS/m) | |
|---|---|---|---|
| Sr. No. | TEMPERATURE (° C.) | Example 1 | Example 2 |
| 1 | 15 | 72.7 | 63.9 |
| 2 | 20 | 73.8 | 64.0 |
| 3 | 25 | 80.6 | 69.8 |
| 4 | 30 | 93.7 | 82.0 |
| 5 | 35 | 100.7 | 84.4 |
| 6 | 40 | 112.9 | 94.6 |

Potential Impact on Other Diesel Properties:

To ensure that other critical properties of diesel are not affected, complete diesel property specification testing is performed.

TABLE 5

Effect of additive on diesel properties

| Test Line No. | Characteristics | Units | Test Method | Specifications Min | Specifications Max | Blank diesel | Example 1 123.25 ppm | Example 2 123.25 ppm |
|---|---|---|---|---|---|---|---|---|
| 1 | COLOUR | — | VISUAL | — | — | Clear | Clear | Clear |
| 2 | DENSITY @15° C. | Kg/m3 | IS 1448 P: 16 | 815.0 | 845.0 | 0.831 | 0.831 | 0.830 |

TABLE 5-continued

Effect of additive on diesel properties

| Test Line No. | Characteristics | Units | Test Method | Specifications Min | Specifications Max | Blank diesel | Example 1 123.25 ppm | Example 2 123.25 ppm |
|---|---|---|---|---|---|---|---|---|
| 3 | WATER CONTENT | mg/Kg | D 4928 | — | 200.0 | 38.6 | 39.4 | 38.4 |
| 4 | 95% V/V RECOVERY | ° C. | IS 1448 P: 18/ISO 3405 | — | 360.0 | 355.4 | 355.1 | 356.0 |
| 5 | KINEMATIC VISCOSITY @40° C. | CSt | IS 1448 P: 25 | 2.000 | 4.500 | 2.711 | 2.718 | 2.703 |
| 2.6 | TOTAL SULFUR | mg/Kg | IS 1448 P: 153 | — | 50 | 4 | 4 | 4 |
| 7 | POUR POINT WINTER | ° C. | IS 1448 P: 10 | — | 3 | −9 | −9 | −9 |
| 8 | FLASH POINT ABEL | ° C. | IS 1448 P: 21 | 66.0 | — | 74.5 | 74.5 | 75.5 |
| 9 | Cu STRIP CORR FOR 3 HRS @ 50° C. | — | IS 1448 P: 15/ISO 2180 | — | 1 | 1a | 1a | 1a |
| 10 | CALCULATED CETANE INDEX | — | ASTM D 4737/ISO 4264 | 46.0 | — | 50 | 50 | 51 |
| 11 | CONDUCTIVITY | pS/m | D2624 | | | 0 | 144.7 | 142 |

From above Table-5, it can be concluded that no other diesel property has been impacted significantly by the addition of the hydrocarbon fuel additive composition(s) as provided by the present invention.

Accordingly, it can be concluded that the polyethyleneamine salt(s) of sulphonyl oleic acid and the hydrocarbon fuel additive composition(s) as provided by the present invention works as a dual functional additive for hydrotreated diesel to improve both lubricity as well as conductivity. The said hydrocarbon fuel additive composition(s) of the present invention shows excellent conductivity and lubricity improvement via a synergistic reinforcement of individual properties.

We claim:

1. A hydrocarbon fuel additive composition comprising:
    a synergistic mixture of
    (i) sulphonyl oleic acid;
    (ii) dioxane; and
    (iii) polyethyleneamine salt of sulphonyl oleic acid.

2. The hydrocarbon fuel additive composition as claimed in claim 1, wherein the composition comprises: (i) 95-99% by weight of sulphonyl oleic acid; (ii) 0.5-2.5% by weight of dioxane; (iii) 0.5-2.5% by weight of polyethyleneamine salt of sulphonyl oleic acid.

3. The hydrocarbon fuel additive composition as claimed in claim 2, wherein the polyethyleneamine salt of sulphonyl oleic acid comprises:
    a sulphonyl oleic acid selected from the group consisting of (9Z)-8-sulfo-octadec-9-enoic acid, (9Z)-11-sulfo-octadec-9-enoic acid, and a combination thereof; and
    at least one polyethyleneamine selected from the group consisting of triethylenetetramine (TETA), diethylenetriamine (DETA), pentamethyldiethylenetriamine, tetraethylenepentamine, 1,4,7-triazacyclononane, and cyclen.

4. The hydrocarbon fuel additive composition as claimed in claim 1, wherein the hydrocarbon fuel additive composition is used for enhancing lubricity and conductivity of hydrocarbon fuel.

5. The hydrocarbon fuel additive composition as claimed in claim 4, wherein the hydrocarbon fuel additive composition is mixed with the hydrocarbon fuel to obtain a hydrocarbon fuel composition with enhanced lubricity and conductivity.

6. The hydrocarbon fuel additive composition as claimed in claim 5, wherein the hydrocarbon fuel is an Ultra Low Sulfur Diesel having sulfur content in a range of 0-10 ppm.

7. A process for preparing a hydrocarbon fuel additive composition, the process comprising:
    preparing at least one polyethyleneamine salt of sulphonyl oleic acid by mixing a sulphonyl oleic acid with at least one polyethyleneamine, wherein sulphonyl oleic acid is 71-75% by volume and at least one polyethyleneamine is 25-29% by volume; and
    mixing (i) 95-99% by weight of a sulphonyl oleic acid; (ii) 0.5-2.5% by weight of dioxane and (iii) 0.5-2.5% by weight of polyethyleneamine salt of a sulphonyl oleic acid to obtain the hydrocarbon fuel additive composition.

8. The process for preparing the hydrocarbon fuel additive composition as claimed in claim 7, wherein the sulphonyl oleic acid is selected from the group consisting of (9Z)-8-sulfo-octadec-9-enoic acid, (9Z)-11-sulfo-octadec-9-enoic acid, and a combination thereof.

9. The process for preparing the hydrocarbon fuel additive composition as claimed in claim 7, wherein the polyethyleneamine is selected from the group consisting of triethylenetetramine (TETA), diethylenetriamine (DETA), pentamethyldiethylenetriamine, tetraethylenepentamine, 1,4,7-triazacyclononane, and cyclen.

10. The hydrocarbon fuel additive composition as claimed in claim 5, wherein the hydrocarbon fuel additive composition has a concentration in a range of 40-125 ppm in the hydrocarbon fuel composition.

* * * * *